(12) United States Patent
Yazawa et al.

(10) Patent No.: US 9,769,877 B2
(45) Date of Patent: Sep. 19, 2017

(54) HEATER CONTROL APPARATUS FOR GAS SENSOR

(71) Applicant: NGK SPARK PLUG CO., LTD., Nagoya-shi, Aichi (JP)

(72) Inventors: Katsunori Yazawa, Kasugai (JP); Tomonori Uemura, Kasugai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 465 days.

(21) Appl. No.: 14/492,932

(22) Filed: Sep. 22, 2014

(65) Prior Publication Data

US 2015/0083703 A1    Mar. 26, 2015

(30) Foreign Application Priority Data

Sep. 24, 2013   (JP) .................................. 2013-196595

(51) Int. Cl.
| H05B 1/02 | (2006.01) |
| G01N 27/407 | (2006.01) |
| G01N 27/406 | (2006.01) |

(52) U.S. Cl.
CPC ......... *H05B 1/0244* (2013.01); *G01N 27/407* (2013.01); *G01N 27/4067* (2013.01)

(58) Field of Classification Search
CPC ................ H05B 1/0244; H05B 1/0236; G01N 27/4067; G01N 27/407; F02D 4/1494
See application file for complete search history.

(56) References Cited

U.S. PATENT DOCUMENTS

| 6,870,142 B2 | 3/2005 | Hada et al. |
| 2002/0179443 A1 | 12/2002 | Hada et al. |
| 2006/0117737 A1* | 6/2006 | Ohsaki ................ F02D 41/0072 60/276 |

FOREIGN PATENT DOCUMENTS

JP       4241737 B2    3/2009

\* cited by examiner

*Primary Examiner* — Shawntina Fuqua
(74) *Attorney, Agent, or Firm* — Sughrue Mion, PLLC (57) ABSTRACT

In a heather control apparatus for a gas sensor, a CPU obtains upper and lower limit values by adding a predetermined value to and subtracting the predetermined value from an Rpvs average obtained in a last heater energization period (or to an Rpvs value obtained for the first time), and sets a window W1. The CPU obtains a plurality of Rpvs values [P2] to [P11], and obtains an Rpvs average A1 while excluding Rpvs values [P5], [P6], and [P9] which do not fall within the window W1 (not less than the lower limit value and not greater than the upper limit value). The CPU obtains the upper and lower limit values by adding the predetermined value to and subtracting the predetermined value from the Rpvs average A1, and sets a window W2 for the next heater energization period.

3 Claims, 5 Drawing Sheets

50: HEATER CONTROL CIRCUIT
71: PID CONTROL CIRCUIT
72: CIRCUIT FOR GENERATING REFERENCE VOLTAGE (450 mV)
73: FIRST DIFFERENTIAL AMPLIFICATION CIRCUIT
82: SECOND DIFFERENTIAL AMPLIFICATION CIRCUIT
83: SAMPLE-AND-HOLD CIRCUIT

HEATER CONTROL APPARATUS FOR GAS SENSOR

BACKGROUND OF THE INVENTION

1. Field of the Invention

The present invention relates to a heater control apparatus for controlling energization of a heater which activates a gas detection element of a gas sensor.

2. Description of the Related Art

A gas sensor has been known which includes a gas detection element having at least one cell composed of a solid electrolyte member and a pair of electrodes, and which detects the concentration of a specific gas such as oxygen. When the temperature of the gas detection element rises, the gas detection element becomes active. Further, the solid electrolyte member exhibits good oxygen-ion conductivity, whereby detection of the concentration of the specific gas becomes possible. The gas detection element is heated by the heat of exhaust gas discharged from an internal combustion engine. Meanwhile, the gas sensor has a heater in order to activate the gas detection element quickly and secure stability of operation by maintaining the gas detection element at a fixed temperature. In general, a control apparatus for the gas sensor controls energization of the heater through PWM (pulse width modulation) control.

The control apparatus for the gas sensor detects the temperature of the gas detection element by detecting the resistance (impedance) thereof while detecting the concentration of the specific gas using the gas detection element. The control apparatus calculates a duty ratio used in the PWM control based on the detected element temperature, and controls energization of the heater to thereby maintain the temperature of the gas detection element constant. If the timing of on/off switching (starting/stopping) of the energization of the heater by the PWM control overlaps with the timing (period) of detection of the element resistance, a signal representing the detected element resistance may contain noise. A control apparatus is known which has solved such a problem by controlling the timing of on/off switching by the PWM control and the timing of detecting the element resistance such that they do not overlap with each other (see, for example, Patent Document 1).

[Patent Document 1] Japanese Patent No. 4241737

3. Problems to be Solved by the Invention

However, in the case of the control apparatus disclosed in Patent Document 1, when the timing of detecting the element resistance and the timing of on/off switching by the PWM control overlap with each other, the timing of detecting the element resistance is shifted or the period of the PWM control is shifted. In the case where the timing of detecting the element resistance is shifted, the control apparatus becomes unable to perform various processes at predetermined intervals and at predetermined timings in order to detect the element resistance. Since the control apparatus must adjust for the various processes in order to cope with changes in the processing timings, a problem arises in that the control becomes complex. Also, in the case where the period of the PWM control is shifted, since the control apparatus must calculate the duty ratio again in order to maintain the element temperature constant, a problem arises in that the control becomes complex.

SUMMARY OF THE INVENTION

The present invention has been made in order to solve the above-described problems, and an object thereof is to provide a heater control apparatus for a gas sensor which can obtain an element resistance while mitigating the influence of noise without changing the timing of detecting the element resistance or the timing of on/off switching by PWM control, and which can control energization of a heater based on the element resistance.

The above object has been achieved by providing a heater control apparatus for a gas sensor which includes a gas detection element having at least one cell composed of a solid electrolyte member and a pair of electrodes provided thereon, and a heater which generates heat upon energization so as to heat and activate the gas detection element, the heater control apparatus controlling energization of the heater in a plurality of energization periods. The heater control apparatus comprises detection means for detecting the resistance of the gas detection element as an element resistance; extraction means for extracting element resistance values which satisfy a predetermined condition from a plurality of element resistance values detected by the detection means; computation means for computing an average of the element resistance values extracted by the extraction means; and heater control means for setting a heater energization duty ratio based on the average computed by the computation means and periodically starting and stopping energization of the heater. The detection means is configured to detect at least four element resistance values within individual energization periods during which the heater is energized by the heater control means, and the computation means is configured to compute the average in individual energization periods within which the heater is energized by the heater control means. The element resistance values which satisfy the predetermined condition are element resistance values which are a portion of the element resistance values detected during a present energization period and which fall within a range having a predetermined value based on the average that is computed by the computation means in a last energization period, or element resistance values which are a portion of the element resistances detected during the present energization period and which remain after exclusion of two element resistance values which are the largest and the second largest in terms of the difference from the average computed by the computation means in the last energization period.

The heater control apparatus for a gas sensor according to the above embodiment can obtain the average of element resistance values used for controlling energization of the heater while excluding an element resistance value(s) which may be influenced by noise or the like. Noise or the like is apt to be generated when energization of the heater is started or stopped. The heater control apparatus can obtain the average of element resistance values accurately, even when the heater control apparatus obtains an element resistance value(s) influenced by noise. Therefore, it is unnecessary to configure the heater control apparatus to obtain the element resistance values while avoiding the timings at which energization of the heater is started and stopped. Therefore, the processing can be simplified. Also, since the heater control apparatus need not detect the timings at which the energization of the heater is started and stopped, the heater control apparatus is always available to perform the operation of obtaining the element resistance.

Also, in the present mode, by excluding element resistance value(s) which do not fall within a range (window) set based on the average (reference) or excluding two element resistance values whose difference from the average are the largest and the second largest, the heater control apparatus can easily exclude an element resistance value(s) which may have been affected by noise or the like and can obtain the average of the element resistances accurately in each of the above-described cases. By controlling energization of the heater using the accurate average of the element resistance values, the heater control apparatus can heat the gas detection element at a proper temperature, and, consequently, can accurately detect the concentration of a specific gas.

DESCRIPTION OF REFERENCE NUMERALS

Reference numerals used to identify various features in the drawings include the following.
10: full-range air-fuel-ratio sensor
30: gas detection element
40: heater
50: heater control circuit
61: CPU
82: second differential amplification circuit
100: ECU

DETAILED DESCRIPTION OF THE PREFERRED EMBODIMENTS

The heater control apparatus for a gas sensor according to the present invention will now be described in greater detail with reference to the drawings. However, the present invention should not be construed as being limited thereto.

In a first embodiment, the gas sensor is a full-range air-fuel-ratio sensor 10, and the heater control apparatus is an electronic control apparatus (ECU) 100 of an automobile. The configurations of the full-range air-fuel-ratio sensor 10 and the ECU 100 will be described with reference to FIG. 1. Notably, since the full-range air-fuel-ratio sensor 10 has a known configuration, the details of its structure, etc., will not be described, and its schematic configuration will be described below.

Figure 1:
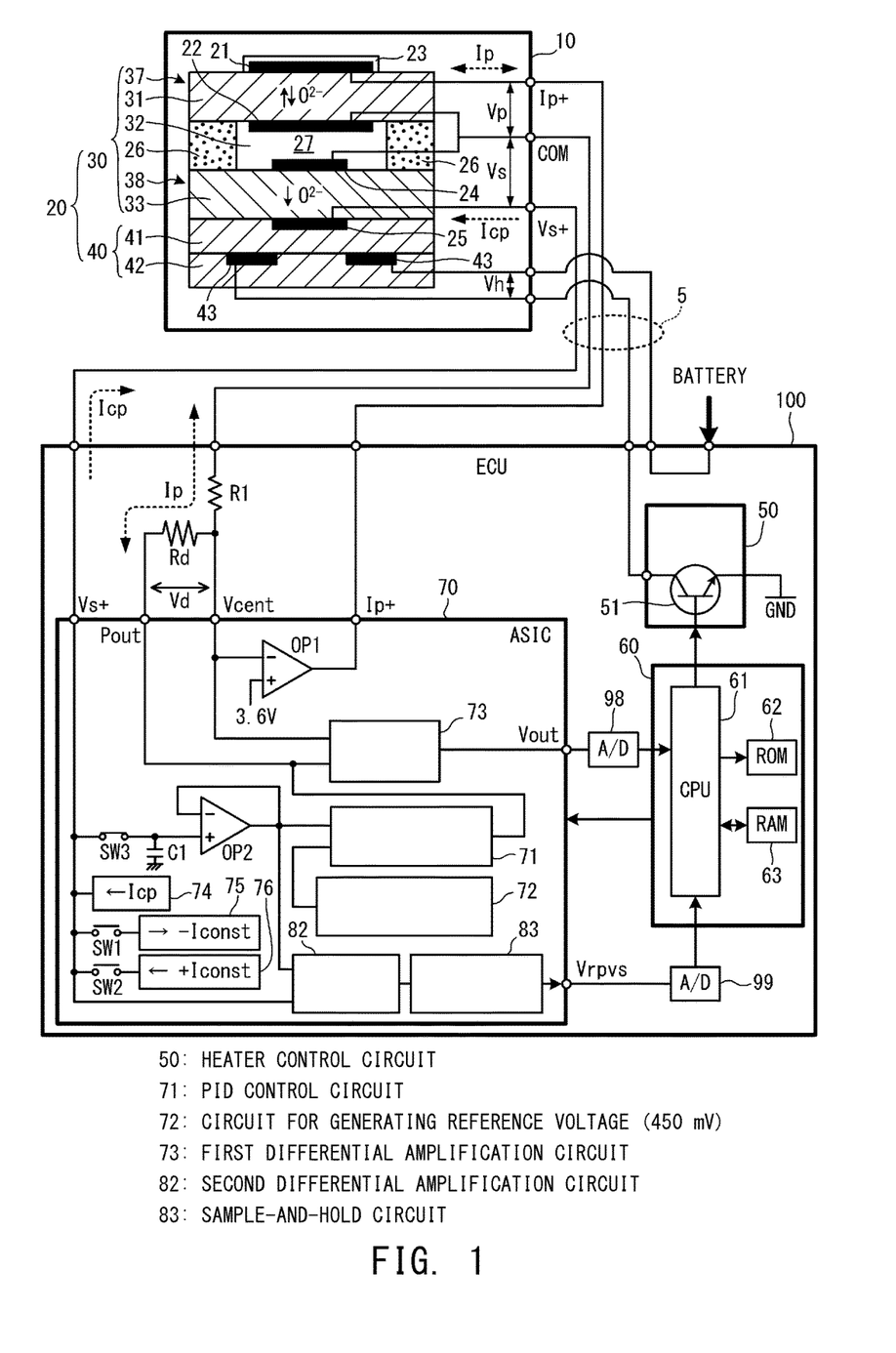
FIG. 1 is a block diagram showing the electrical configuration of a full-range air-fuel-ratio sensor 10 having a heater 40 and the electrical configuration of an ECU 100.

The full-range air-fuel-ratio sensor 10 shown in FIG. 1 is a sensor which is attached to an exhaust passage (not shown) of an engine of an automobile and which detects the air-fuel ratio of exhaust gas flowing through the exhaust passage based on the oxygen concentration of the exhaust gas. The full-range air-fuel-ratio sensor 10 has an unillustrated housing and a narrow, elongated plate-shaped sensor element 20 held within the housing. The full-range air-fuel-ratio sensor 10 has a plurality of lead wires 5 for supplying electric current to the sensor element 20. The lead wires 5 extend outside the sensor 10 and are electrically connected to the ECU 100 disposed at a remote location. The ECU 100 includes a microcomputer 60, and an application specific integrated circuit (ASIC) 70 and a heater control circuit 50 are incorporated therein. The ECU 100 controls the supply of electric current to the full-range air-fuel-ratio sensor 10 using the ASIC 70 and the heater control circuit 50, and performs air-fuel ratio feedback control for the engine based on an output obtained from the full-range air-fuel-ratio sensor 10.

The structure of the sensor element 20 will now be described. The sensor element 20 is formed by uniting a gas detection element 30 for detecting the oxygen concentration of exhaust gas and a heater 40 for heating the gas detection element 30. The gas detection element 30 includes solid electrolyte members 31 and 33 mainly formed of zirconia and an insulating substrate 32 mainly formed of alumina. Each of the solid electrolyte members 31 and 33 and the insulating substrate 32 has the shape of a narrow, elongated plate. The gas detection element 30 has a structure in which the solid electrolyte member 33, the insulating substrate 32, and the solid electrolyte member 31 are stacked in this order in the thickness direction. Notably, FIG. 1 shows a cross section of the solid electrolyte members 31 and 33 and the insulating substrate 32 taken perpendicular to the longitudinal direction of the sensor element 20. The solid electrolyte member 31 has a pair of electrodes 21 and 22 which are mainly made of platinum and are formed on opposite surfaces of the solid electrolyte member 31. The surface of the electrode 21 is covered with a porous protection layer 23 formed of ceramic. The protection layer 23 protects the electrode 21 from poisoning components (e.g., silicon) contained in exhaust gas. The solid electrolyte member 33 has a pair of electrodes 24 and 25 formed on opposite surfaces thereof. The electrode 25 is sandwiched between the solid electrolyte member 33 and an insulating layer 41 (described below).

The insulating substrate 32 has a hollow gas detection chamber 27 which is formed at one end thereof in the longitudinal direction and whose opposite side walls in the thickness direction are formed by the solid electrolyte members 31 and 33. The gas detection chamber 27 has porous diffusion-rate-limiting portions 26 at opposite ends thereof in the width direction. Exhaust gas can be introduced into the gas detection chamber 27 through the diffusion-rate-limiting portions 26. The diffusion-rate-limiting portions 26 limit the flow rate of exhaust gas introduced into the gas detection chamber 27. The electrode 22 on the solid electrolyte member 31 and the electrode 24 on the solid electrolyte member 33 are exposed to the interior of the gas detection chamber 27.

The heater 40 includes two insulating layers 41 and 42 which are mainly formed of alumina, which have the shape of a narrow, elongated plate similar to the shape of the solid electrolyte members, and which are stacked in the thickness direction. A heat generation resistor 43 mainly formed of platinum is disposed between the insulating layers 41 and 42. Solid electrolyte members formed of zirconia exhibit an insulating property at ordinary temperature, but become active and exhibit oxygen ion conductivity under a high-temperature environment. The heater 40 is provided so as to heat and activate the solid electrolyte members 31 and 33 and to stabilize the oxygen ion conductivity after the activation. The heater 40 is united with the gas detection element 30 so as to constitute the sensor element 20 such that the insulating layer 41 is disposed on the outer side of the solid electrolyte member 33 of the gas detection element 30.

In the sensor element 20 having the above-described structure, the solid electrolyte member 31 and the pair of electrodes 21 and 22 provided on the opposite surfaces thereof function as an oxygen pump cell which pumps oxygen into the gas detection chamber 27 from outside the sensor element 20 or pumps out oxygen from the gas detection chamber 27 to the outside. In the following description, the oxygen pump cell composed of the solid electrolyte member 31 and the electrodes 21 and 22 will be referred to as an Ip cell 37. The solid electrolyte member 33 and the pair of electrodes 24 and 25 provided on the opposite surfaces thereof function as an oxygen concentration detection cell which generates electromotive force in accordance with a difference in oxygen concentration between the two electrodes. When a very small constant current Icp is supplied so as to flow between the pair of electrodes 24 and 25, the electrode 25 produces a reference oxygen source. Namely, the electrode 25 is exposed to a reference oxygen concentration atmosphere which serves as a reference for detection of oxygen concentration by the oxygen concentration detection cell, and acts as a reference electrode. In the following description, the oxygen concentration detection cell composed of the solid electrolyte member 33 and the electrodes 24 and 25 will be referred to as a Vs cell 38. Of the electrodes of the Ip cell 37 and the Vs cell 38, one electrode 22 of the Ip cell 37 and one electrode 24 of the Vs cell 38 exposed to the gas detection chamber 27 are electrically connected to each other and to a COM port of the full-range air-fuel-ratio sensor 10. The other electrode 25 of the Vs cell 38 is connected to a Vs+ port, and the other electrode 21 of the Ip cell 37 is connected to an Ip+ port.

Next, the schematic configuration of the ECU 100 to which the sensor element 20 is connected will be described. The ECU 100 includes the microcomputer 60, the ASIC 70, and the heater control circuit 50. Although not shown, the ECU 100 includes various other circuits (devices) for engine control in addition to those shown in the drawing.

The microcomputer 60 is a device for electronically controlling the drive of the engine of the automobile, etc. The microcomputer 60 controls circuits (devices), including the ASIC 70, connected to the microcomputer 60 by executing various control programs, to thereby control fuel injection timing and ignition timing. The microcomputer 60 controls the supply of electric power to the full-range air-fuel-ratio sensor 10 through the ASIC 70 and the heater control circuit 50, and obtains a current value corresponding to the oxygen concentration of exhaust gas from the sensor element 20 as a voltage signal. Further, the microcomputer 60 obtains other information such as crank angle (used for detection of the piston position and rotational speed of the engine) and combustion pressure from other circuits (devices). The microcomputer 60 includes a CPU 61, a ROM 62, and a RAM 63, each having a known configuration. The CPU 61 executes various controls including the above-described control. The ROM 62 stores programs for performing the various controls, initial values, etc. The RAM 63 temporarily stores variables, flags, counters, etc., used for execution of the programs.

The ASIC 70 is an application specific integrated circuit in which circuits for driving and controlling the full-range air-fuel-ratio sensor 10 are integrated into a single chip to thereby allow the circuits to be easily incorporated into the ECU 100. The ASIC 70 supplies electric power to the gas detection element 30 in accordance with a signal input from the microcomputer 60, and outputs to the microcomputer 60 the oxygen concentration detected by the gas detection element 30. Specifically, the ASIC 70 supplies a very small constant current Icp to the Vs cell 38 of the gas detection element 30 so as to cause oxygen ions to move toward the electrode 25 and to accumulate oxygen there. Thus, the electrode 25 functions as a reference electrode. The ASIC 70 detects the electromotive force Vs generated between the pair of electrodes 24 and 25 of the Vs cell 38, and compares it with a predetermined reference voltage (e.g., 450 mV). The ASIC 70 controls the flow direction and magnitude of the pump current Ip flowing between the pair of electrodes 21 and 22 of the Ip cell 37 based on the comparison result. The Ip cell 37 pumps oxygen into the gas detection chamber 27 or pumps out oxygen from the gas detection chamber 27 in accordance with the flow direction and magnitude of the pump current Ip. Further, the ASIC 70 separately detects a change in the resistance of the gas detection element 30 which changes with temperature, and outputs the detected change to the microcomputer 60.

The heater control circuit 50 applies a voltage Vh from a battery to opposite ends of the heat generation resistor 43 of the heater 40. The heater control circuit 50 includes a switching device 51 for controlling the supply of electric current to the heat generation resistor 43 by PWM control (pulse width modulation control). The duty ratio of the voltage waveform of the voltage Vh applied to opposite ends of the heat generation resistor 43 is calculated by the CPU 61 of the microcomputer 60. Specifically, the CPU 61 computes the duty ratio based on the change in resistance which is detected by the ASIC 70 and corresponds to the heated state of the Vs cell 38. The CPU 61 outputs a pulse signal to the heater control circuit 50 in accordance with the computed duty ratio. On the basis of the pulse signal output from the CPU 61, the heater control circuit 50 applies the voltage Vh to the heat generation resistor 43, the voltage Vh having a voltage waveform corresponding to the duty ratio, to thereby heat the Ip cell 37 and the Vs cell 38.

The ECU 100 further includes A/D converters 98 and 99, a resistor R1, and a detection resistor Rd. The A/D converters 98 and 99 are connected to Vout and Vrpvs ports (described below) of the ASIC 70, respectively. The A/D converters 98 and 99 convert analog output voltages supplied from the respective ports to digital data, and output the digital data to the CPU 61 of the microcomputer 60.

Next, the electrical configuration of the ASIC 70 will be described. The ASIC 70 has a plurality of input/output ports (Vs+, Pout, Vcent, Ip+, Vout, Vrpvs). The Vs+ and Ip+ ports of the full-range air-fuel-ratio sensor 10 are connected to the Vs+ and Ip+ ports, respectively, of the ASIC 70 through the lead wires 5. The COM port of the full-range air-fuel-ratio sensor 10 is connected to the resistor R1 of the ECU 100 through the lead wires 5, and is also connected to the Vcent and Pout ports of the ASIC 70 through the resistor R1 and the detection resistor Rd.

The ASIC 70 includes a PID control circuit 71, a reference voltage generation circuit 72, a first differential amplification circuit 73, an Icp supply circuit 74, a switch SW1, a −Iconst supply circuit 75, a switch SW2, a +Iconst supply circuit 76, a second differential amplification circuit 82, a sample-and-hold circuit 83, an operational amplifier OP1, a buffer OP2, a switch SW3, and a capacitor C1. The Icp supply circuit 74 is a circuit for supplying a very small constant current Icp to the gas detection element 30 of the full-range air-fuel-ratio sensor 10. The −Iconst supply circuit 75 is a circuit for supplying a constant current −Iconst which is set to a predetermined current value for measuring the resistance of the Vs cell 38, and the +Iconst supply circuit 76 is a circuit for supplying a constant current +Iconst which is set to a predetermined current value of a polarity opposite the polarity of the constant current −Iconst. The Icp supply circuit 74, the −Iconst supply circuit 75, and the +Iconst supply circuit 76 are connected to the Vs+ port. The operational amplifier OP1 supplies the pump current Ip to the Ip cell 37 of the gas detection element 30. The output terminal of the operational amplifier OP1 is connected to the Ip+ port.

The inverted input (−) terminal of the operational amplifier OP1 is connected to the Vcent port, and a reference voltage of 3.6 V is applied to the non-inverted input (+) terminal of the operational amplifier OP1.

The PID control circuit 71 controls the magnitude of the pump current Ip supplied from the operational amplifier OP1 to the Ip cell 37. The input side of the PID control circuit 71 is connected to the Vs+ port through the buffer OP2. Specifically, the non-inverted input (+) terminal of the buffer OP2 is connected to the Vs+ port through the switch SW3, and the capacitor C1 is connected to a line extending between the non-inverted input (+) terminal and the switch SW3. The output terminal of the buffer OP2 is connected to the inverted input (−) terminal of the buffer OP2 and the input side of the PID control circuit 71. Also, the input side of the PID control circuit 71 is connected to the reference voltage generation circuit 72. The reference voltage generation circuit 72 generates a reference voltage (450 mV) which serves as a target used for controlling the pump current Ip. The output side of the PID control circuit 71 is connected to the Pout port, and is also connected to the Vcent port, that is, the inverted input (−) terminal of the operational amplifier OP1, through the detection resistor Rd. The detection resistor Rd is a resistor for detecting the magnitude of the pump current Ip. The opposite ends of the detection resistor Rd are connected to the Pout port and the Vcent port. The Pout port and the Vcent port are connected to the input side of the first differential amplification circuit 73. The first differential amplification circuit 73 is a circuit for amplifying, at a predetermined amplification factor, a potential difference Vd which is generated across the detection resistor Rd as a result of the pump current Ip flowing therethrough. The first differential amplification circuit 73 has a known circuit configuration including an operational amplifier and resistors. The first differential amplification circuit 73 outputs the amplified potential difference Vd, as a detected potential Vout, from the Vout port to the microcomputer 60 through the A/D converter 98.

The output terminal of the buffer OP2 is also connected to the input side of the second differential amplification circuit 82. The input side of the second differential amplification circuit 82 is connected to the Vs+ port, is connected to the −Iconst supply circuit 75 through the switch SW1, and is connected to the +Iconst supply circuit 76 through the switch SW2. The output side of the second differential amplification circuit 82 is connected to the input side of the sample-and-hold circuit 83. The output side of the sample-and-hold circuit 83 is connected to the Vrpvs port, whereby the output of the second differential amplification circuit 82 is output to the microcomputer 60 through the A/D converter 99. As described below, the microcomputer 60 obtains the element resistance (Rpvs) of the Vs cell 38 so as to perform control for maintaining the temperature of the gas detection element 30 constant. The detection of the Rpvs value is performed based on a change in the voltage Vs produced across the Vs cell 38 when the constant current −Iconst for resistance measurement is supplied to the Vs cell 38. The second differential amplification circuit 82 is a circuit for detecting a potential difference ΔVs between the potential of the Vs+ port before supply of the constant current −Iconst and the potential of the Vs+ port after the constant current −Iconst has been supplied for a predetermined time. The second differential amplification circuit 82 has a known circuit configuration including an operational amplifier and resistors. The sample-and-hold circuit 83 has a known circuit configuration for holding the potential difference ΔVs output from the second differential amplification circuit 82.

The sample-and-hold circuit 83 functions to hold the potential difference ΔVs detected at a given time until the next time the potential difference ΔVs is detected, and adjusts the timing of reading by the CPU 61.

Although not illustrated, the ASIC 70 includes a plurality of switches other than the switches SW1 to SW3, and includes a switch control circuit for turning the switches on and off. The switch control circuit switches the states of the switches between on and off states in accordance with the selected one of various control modes of the gas detection element 30 to thereby control the drive/non-drive of the above-described various circuits. For example, in a non-active mode in which the gas detection element 30 is to be activated, the gas detection element 30 is heated by energizing the heater 40. At this time, the switch control circuit turns on the switch for the Icp supply circuit 74 so as to allow the supply of current from the Icp supply circuit 74, and turns off the switches for the PID control circuit 71 and the operational amplifier OP1 so as to interrupt the supply of the output of the PID control circuit 71 and the supply of the output of the operational amplifier OP1. As a result, a constant current Icp is supplied to the Vs cell 38, and oxygen is accumulated at the reference electrode (the electrode 25). In an active mode in which the gas detection element 30 is active and the oxygen concentration is detected, the switch control circuit turns on the switch for the Icp supply circuit 74 so as to allow the supply of current from the Icp supply circuit 74, and turns on the switches for the PID control circuit 71 and the operational amplifier OP1 so as to allow the supply of the output of the PID control circuit 71 and the supply of the output of the operational amplifier OP1. As a result, it becomes possible to supply a large current Ip for detecting the oxygen concentration from the PID control circuit 71 and the operational amplifier OP1 to the Ip cell 37 in a state in which the supply of the constant current Icp to the Vs cell 38 is maintained.

In the active mode, a control for a detection mode which obtains the element resistance of the Vs cell 38 is performed periodically. In the detection mode, the switch control circuit turns on the switch SW1 for a predetermined short period of time so as to allow the supply of current from the −Iconst supply circuit 75, and turns off the switch SW3 so as to break the connection between the Vs+ port and the non-inverted input (+) terminal of the buffer OP2. The constant current Icp and the constant current −Iconst superimposed thereon are supplied to the Vs cell 38, and the potential generated at the Vs+ port is input to the second differential amplification circuit 82. When the switch SW3 is tuned off, the capacitor C1 maintains the potential at the Vs+ port at the time when only the constant current Icp had been supplied, and inputs that potential to the second differential amplification circuit 82 through the buffer OP2. The second differential amplification circuit 82 outputs the potential difference ΔVs between the potential at the Vs+ port at a point in time immediately before supply of the constant current −Iconst to the Vs cell 38 and the potential at the Vs+ port which has changed as a result of the supply of the constant current −Iconst. The potential difference ΔVs is supplied to the Vrpvs port via the sample-and-hold circuit 83, and is sent from the Vrpvs port to the microcomputer 60 through the A/D converter 99. The CPU 61 of the microcomputer 60 computes the element resistance (Rpvs) of the Vs cell 38 based on the potential difference ΔVs. As described below, during execution of Rpvs computation processing, the CPU 61 obtains a plurality of Rpvs values, and computes an Rpvs average used for calculating the duty ratio used in the PWM control for the heater control circuit 50.

Notably, the constant current −Iconst is supplied to the Vs cell 38 for a predetermined short period of time. However, after the switch control circuit stops the supply of current from the constant current −Iconst supply circuit 75 by turning off the switch SW1, the potential difference ΔVs output from the second differential amplification circuit 82 is held by the sample-and-hold circuit 83. Next, the switch control circuit turns on the switch SW2 so as to allow the +Iconst supply circuit 76 to supply the constant current +Iconst of opposite polarity to the Vs cell 38. This operation is performed so as to cause the Vs cell 38 to recover, within a short period of time, from a state in which the Vs cell 38 does not output an internal electromotive force reflecting the true oxygen concentration difference due to polarization. After having obtained the potential difference ΔVs, the switch control circuit returns the on-off states of the switches SW1 to SW3 to the original states for the active mode. Notably, even in the non-active mode, the control for the detection mode is performed, and the determination as to whether the gas detection element 30 is active or not is performed based on the Rpvs value.

Next, an operation of detecting the oxygen concentration (air-fuel ratio) of exhaust gas using the full-range air-fuel-ratio sensor 10 will be described briefly. First, the voltage (electromotive force) Vs generated between the pair of electrodes 24 and 25 of the Vs cell 38 is compared with 450 mV which is set as a control target voltage for the voltage Vs for causing the air-fuel ratio of the exhaust gas within the gas detection chamber 27 to approach the theoretical air-fuel ratio, and the comparison result is supplied to the operational amplifier OP1 as a feedback. Namely, the flow direction and magnitude of the pump current Ip flowing through the Ip cell 37 are controlled by the PID control circuit 71 and the operational amplifier OP1, whereby the pumping in or out of oxygen by the Ip cell 37 is performed such that the air-fuel ratio of the exhaust gas within the gas detection chamber 27 becomes equal to the theoretical air-fuel ratio.

Specifically, in the case where the air-fuel ratio of the exhaust gas having flowed into the gas detection chamber 27 is on the rich side in relation to the theoretical air-fuel ratio, the oxygen concentration of the exhaust gas is low. Therefore, the pump current Ip is controlled such that oxygen is pumped into the gas detection chamber 27 from outside the sensor element 20 through the solid electrolyte member 31. Meanwhile, in the case where the air-fuel ratio of the exhaust gas having flowed into the gas detection chamber 27 is on the lean side in relation to the theoretical air-fuel ratio, a large amount of oxygen is present in the exhaust gas. Therefore, the pump current Ip is controlled such that oxygen is pumped out from the gas detection chamber 27 to the outside. The pump current Ip at that time flows through the detection resistor Rd. The first differential amplification circuit 73 converts the pump current Ip (the potential difference between the opposite ends of the detection resistor Rd) to a voltage signal, and outputs it to the CPU 61 of the microcomputer 60 through the A/D converter 98 as the output (detection signal) of the full-range air-fuel-ratio sensor 10. The CPU 61 detects the oxygen concentration of the exhaust gas (consequently, the air-fuel ratio of the exhaust gas) from the flow direction and magnitude of the pump current Ip obtained as a detection signal.

In order to stably detect the oxygen concentration, it is necessary to perform a control for activating the gas detection element 30 by heating it until the temperatures of the solid electrolyte members 31 and 33 become equal to or higher than an activation temperature (e.g., 750° C.) and maintaining the temperature of the activated gas detection element 30 constant after the activation. As described above, the heater control circuit 50 controls the supply of electric current to the heat generation resistor 43 of the heater 40 for heating the gas detection element 30 by PWM control in accordance with the duty ratio calculated by the CPU 61 of the microcomputer 60. Since the battery voltage is applied to the heater 40, noise may be generated when the supply of electric current to the heater 40 is started or stopped by the PWM control. Also, the ECU 100 may be influenced by external noise. When noise is produced, the reference potential of the ECU 100 changes.

As described above, the element resistance (Rpvs) of the Vs cell 38 is obtained based on the potential difference ΔVs which is a change in potential produced at the Vs+ port as a result of supply of the constant current −Iconst for a predetermined short period of time. The potential difference ΔVs is detected by the second differential amplification circuit 82 and is held by the sample-and-hold circuit 83 such that the CPU 61 can obtain the potential difference ΔVs at a predetermined timing. Therefore, when the Rpvs value is affected by noise, depending on the timing at which the noise is generated, the Rpvs value may become higher or lower than the true Rpvs value which includes no noise. Namely, in some cases, both the Rpvs value on which noise generated as a result of starting energization of the heater 40 has been superimposed and the Rpvs value on which noise generated as a result of stopping energization of the heater 40 has been superimposed become larger or smaller than the true element resistance Rpvs. In other cases, the Rpvs value on which noise generated as a result of starting energization of the heater 40 has been superimposed and the Rpvs value on which noise generated as a result of stopping energization of the heater 40 has been superimposed become larger and smaller, respectively, than the true element resistance Rpvs.

For example, a case is considered where the influence of noise is absent at the time when the sample-and-hold circuit 83 holds the potential difference ΔVs. When the potential difference ΔVs is output to the CPU 61, the heater 40 turns on and the reference potential increases. In such a case, the element resistance Rpvs obtained by the CPU 61 may become smaller than the true element resistance Rpvs. Also, the element resistance Rpvs obtained by the CPU 61 may become larger than the true element resistance Rpvs, for example, in the case where the supply of electric current to the heater 40 is started, the potential difference ΔVs becomes larger than the true potential difference due to the influence of instantaneous noise generated at that time, and that value is held by the sample-and-hold circuit 83. However, the potential difference ΔVs is output to the CPU 61 before the reference potential increases due to the influence of noise. Also, the element resistance Rpvs obtained by the CPU 61 may become larger than the true element resistance Rpvs. For example, in the case where the supply of electric current to the heater 40 is stopped, a value larger than the true potential difference ΔVs is held by the sample-and-hold circuit 83 due to the influence of instantaneous noise generated at that time. However, the reference potential decreases because of disappearance of the influence on the reference potential when the potential difference ΔVs is output to the CPU 61. Depending on the timing at which the noise is generated, the influence of the noise is not exerted on the potential difference ΔVs even when the reference potential changes. Namely, if the reference potential changes such that the reference potential at the time when the sample-and-hold circuit 83 holds the potential difference ΔVs becomes the same as the reference potential at the time when the sample-and-hold circuit 83 outputs the potential difference ΔVs to the CPU 61, the influence of the noise is not exerted on the potential difference ΔVs, which is the differential value.

In view of the above, in the first embodiment, the CPU 61 performs the Rpvs computation processing to thereby obtain the element resistance (Rpvs) of the Vs cell 38 a plurality of times during each period (PWM control period) within which the heater 40 is energized one time. The CPU 61 calculates the average of the Rpvs values (the Rpvs average) for the present PWM control period after eliminating an Rpvs value(s) which falls outside a window (an allowable range of resistance defined by an upper limit value and a lower limit value) that is set based on the Rpvs average obtained in the last PWM control period and which may contain noise superimposed thereon. Namely, the CPU 61 can eliminate an Rpvs value(s) on which noise has been superimposed even in the case where both the Rpvs value on which noise generated as a result of starting energization of the heater 40 has been superimposed and the Rpvs value on which noise generated as a result of stopping energization of the heater 40 has been superimposed become larger or smaller than the true element resistance Rpvs. Also, in the case where the Rpvs value on which noise generated as a result of starting energization of the heater 40 has been superimposed and the Rpvs value on which noise generated as a result of stopping energization of the heater 40 has been superimposed become larger and smaller, respectively, than the true element resistance Rpvs. The CPU 61 calculates the duty ratio for the PWM control based on the Rpvs average obtained as described above, and causes the heater control circuit 50 to apply the voltage Vh, which has a voltage waveform corresponding to the duty ratio, to the heat generation resistor 43, to thereby maintain the temperature of the gas detection element 30 constant.

The Rpvs computation processing of the first embodiment will now be described with reference to FIGS. 2 and 3. Notably, a program for the Rpvs computation processing is stored in the ROM 62, and is read and executed by the CPU 61. The CPU 61 sets a work area in the RAM 63 so as to secure a memory area for the Rpvs values, a buffer for average computation, a cumulating counter, the window (upper and lower limit values), the Rpvs average, a Rpvs timer, and a PWM timer. In the first embodiment, the PWM control period of the heater 40 is, for example, 100 ms, and the CPU 61 obtains the Rpvs value at an interval of, for example, 10 ms.

No window is set before the program for the Rpvs computation processing is executed the first time. As shown in FIG. 3, only when the CPU 61 executes the program a first time, the CPU 61 obtains an Rpvs value [P1] one time, obtains upper and lower limit values by adding a predetermined value to the obtained Rpvs value and subtracting the predetermined value from the obtained Rpvs value, and sets a window W1. Also, the CPU 61 starts the Rpvs timer for clocking the interval (10 ms) at which the Rpvs value is obtained, and the PWM timer for clocking the PWM control period (100 ms) of the heater 40. Also, the CPU 61 clears the buffer for average computation and the cumulating counter so as to store 0 therein. Notably, it is assumed that the duty ratio used in the PWM control for the heater 40 is 0.4.

Figure 2:
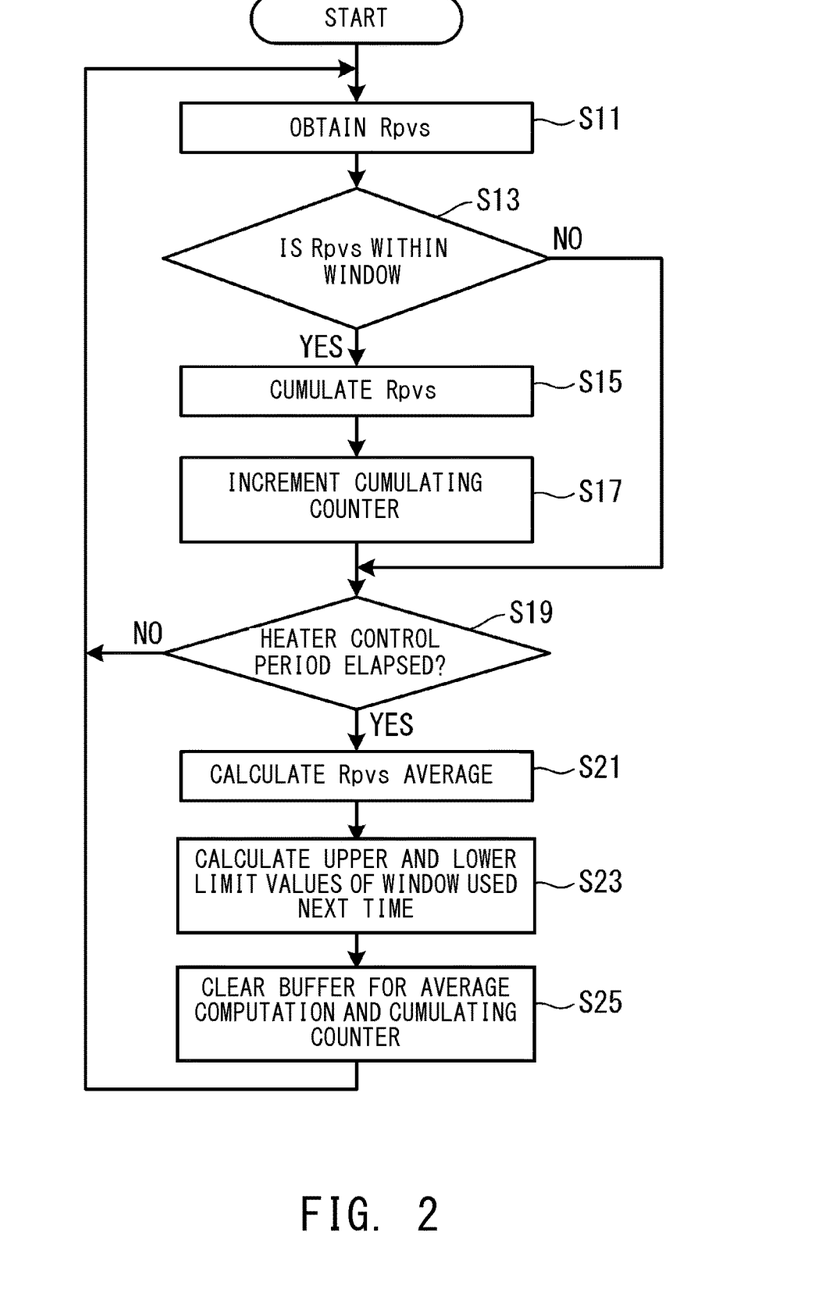
FIG. 2 is a flowchart of Rpvs computation processing (window scheme).

As shown in FIG. 2, the CPU 61 reads the potential difference ΔVs held by the sample-and-hold circuit 83 of the ASIC 70 through the A/D converter 99, and obtains an Rpvs value [P2] based on the potential difference ΔVs (see FIG. 3) (S11). The potential difference ΔVs is the difference between the potential at the Vs+ port at the time when the constant current Icp is supplied and the potential at the Vs+ port at the time when the constant current Icp and the constant current −Iconst superimposed thereon are supplied. Therefore, the CPU 61 calculates the Rpvs value [P2] by the expression of ΔVs/(−Iconst), and stores it in the RAM 63. Notably, the CPU 61 obtains the Rpvs value when the Rpvs timer has clocked the interval of obtaining the Rpvs value, and restarts the Rpvs timer.

The CPU 61 determines whether or not the obtained Rpvs value [P2] falls within the window W1 (S13). The window is set as follows. By the processing of S23, a predetermined amount is added to the Rpvs average obtained by the processing of S21 (described below) so as to obtain an upper limit value, and the predetermined amount is subtracted from the Rpvs average so as to obtain a lower limit value, whereby the window is set. Since no window has been set before the program for the Rpvs computation processing is executed a first time, the window is set based on the Rpvs value [P1] obtained first time (see FIG. 3). When the Rpvs value [P2] falls within the window W1 (is not greater than the upper limit value and not less than the lower limit value) (S13: YES), the CPU 61 adds the Rpvs value [P2] to the buffer for average computation secured in the RAM 63 (S15). Also, the CPU 61 increments the cumulating counter (see FIG. 3) by adding one to the count value of the cumulating counter (S17).

The CPU 61 determines whether or not the PWM control period of the heater 40 has elapsed based on the value of the PWM timer (S19). When the PWM control period has not yet elapsed (S19: NO), the CPU 61 returns to S11. Until the PWM control period elapses, the CPU 61 repeats the processing of S11 to S19 to thereby obtain the Rpvs value and determine whether the Rpvs value falls within the window W1 in the same manner as described above. As shown in FIG. 3, the Rpvs values [P3] and [P4] obtained after elapse of 20 ms and 30 ms following the start of the PWM timer fall within the window W1. The CPU 61 adds these values to the buffer for average computation, and increments the cumulating counter.

After elapse of 40 ms following the start of the PWM timer, the timing of obtaining the element resistance overlaps (coincides) with the timing at which energization of the heater 40 is stopped, whereby noise is superimposed on the obtained Rpvs value [P5]. In such a case, the Rpvs value [P5] falls outside the window W1. As shown in FIG. 2, when the Rpvs value [P5] falls outside the window W1 (S13: NO), the CPU 61 proceeds to S19. The CPU 61 does not add the Rpvs value [P5] to the buffer for average computation, and does not increment the cumulating counter. Namely, the CPU 61 excludes the Rpvs value [P5] from the Rpvs values used for calculating the Rpvs average. In the case where the Rpvs value [P6] (FIG. 3) obtained after elapse of 50 ms following the start of the PWM timer is also influenced by noise generated as a result of stopping energization of the heater 40 and falls outside the window W1, the CPU 61 excludes the Rpvs value [P6] as well from the Rpvs values used for calculating the Rpvs average. In the case where the Rpvs value [P9] (FIG. 3) obtained after elapse of 80 ms following the start of the PWM timer is influenced, for example, by external noise and falls outside the window W1, similarly, the CPU 61 excludes the Rpvs value [P9] from the Rpvs values used for calculating the Rpvs average.

If the Rpvs value [P11] obtained after elapse of 100 ms following the start of the PWM timer falls within the window W1, the CPU 61 adds the Rpvs value [P11] to the buffer for average computation (S15), and increments the cumulating counter (S17). When the CPU 61 determines based on the value of the PWM timer that the PWM control period has elapsed (S19: YES), the CPU 61 restarts the PWM timer, and calculates the Rpvs average (S21). The Rpvs average is obtained by dividing the total of the Rpvs values added to the buffer for average computation by the value of the cumulating counter. As shown in FIG. 3, the Rpvs values used for calculating the Rpvs average A1 are seven Rpvs values; i.e., [P2] to [P4], [P7], [P8], [P10], and [P11]. The CPU 61 stores the calculated Rpvs average A1 in the RAM 63. Also, the CPU 61 copies the Rpvs average A1 to a predetermined memory area of the RAM 63 so as to allow another program which is executed by the CPU 61 for PWM control of the heater 40 to utilize the Rpvs average A1. The CPU 61 obtains the upper limit value by adding a predetermined value to the Rpvs average A1, obtains the lower limit value by subtracting the predetermined value from the Rpvs average A1, and sets a window W2 used for the next PWM control period (S23). The CPU 61 clears the buffer for average computation and the cumulating counter to thereby store 0 therein (S25), and returns to S11.

After that, in the same manner as described above, the CPU 61 obtains a plurality of Rpvs values in each PWM control period, excludes the values falling outside the window, and obtains the Rpvs average for the present PWM control period. When the CPU 61 executes another program, it calculates the duty ratio for the PWM control based on the Rpvs average. The CPU 61 controls the heater control circuit 50 to apply to the heat generation resistor 43 of the heater 40 a voltage Vh having a waveform corresponding to the duty ratio to thereby maintain the temperature of the gas detection element 30 constant. Since the Rpvs average is obtained from a plurality of Rpvs values during each PWM control period from which an Rpvs value(s) influenced by noise has been removed, the accuracy of the Rpvs average is high, and the CPU 61 can control the temperature of the gas detection element 30 accurately.

Figure 3:
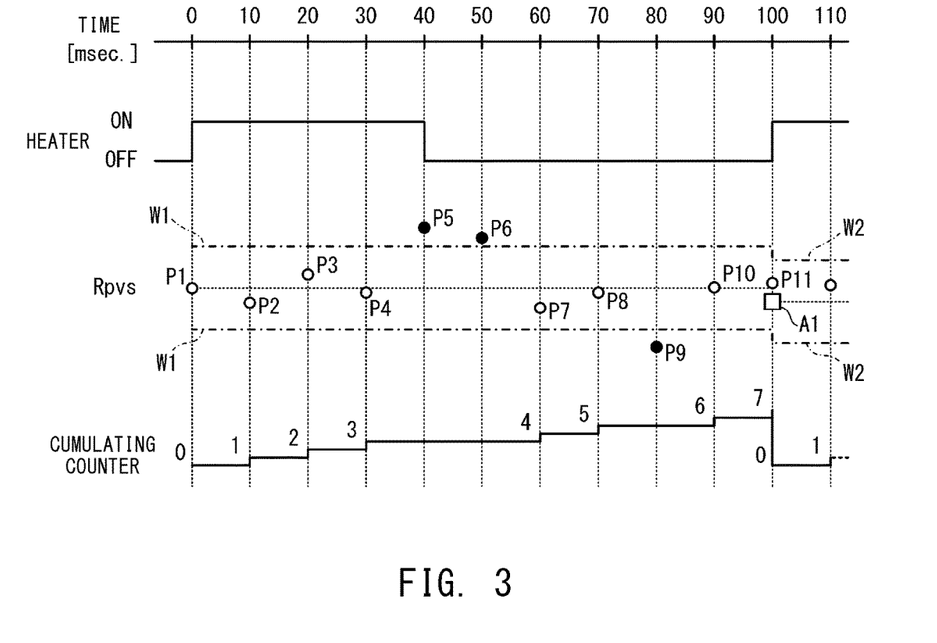
FIG. 3 is a timing chart used for describing the Rpvs computation processing (window scheme).

Notably, as in the example of FIG. 3, the Rpvs value may be influenced by external noise in some cases. However, from the viewpoint of securing accuracy of the Rpvs average, it is sufficient to consider the case where the Rpvs value is influenced by noise generated when energization of the heater 40 is started and stopped. Also, in the example of FIG. 3, the Rpvs values [P5] and [P6] are considered to have been influenced by noise generated when the energization of the heater 40 is stopped. However, it is rare that each of the noises generated when the energization of the heater 40 is started and stopped, respectively, affects the Rpvs value over two Rpvs obtaining intervals. Therefore, considering the fact that in some cases the respective noises generated when energization of the heater 40 is started and stopped affects the Rpvs value in a given PWM control period, it is sufficient for the CPU 61 to obtain at least four Rpvs values and compute a single Rpvs average for each PWM control period.

Next, a second embodiment of the heater control apparatus will be described. Like the first embodiment, the heater control apparatus of the second embodiment is the ECU 100 for controlling the full-range air-fuel-ratio sensor 10. The second embodiment differs from the first embodiment in the specifics of the Rpvs computation processing. Therefore, in the following description, explanation of the mechanical configuration of the heater control apparatus is omitted, and only the Rpvs computation processing will be explained.

In the second embodiment, the CPU 61 performs the Rpvs computation processing to thereby obtain the element resistance (Rpvs) of the Vs cell 38 a plurality of times during each period (PWM control period) within which the heater 40 is energized one time. The CPU 61 calculates the average of the Rpvs values (the Rpvs average) for this PWM control period after excluding two Rpvs values whose differences (deviations) from the Rpvs average obtained in the last control period are the largest and the second largest and on which noise may be superimposed. Noise is likely to be generated when energization of the heater 40 is started or stopped, and there is a possibility that noise is superimposed on two of a plurality of Rpvs values obtained during a single PWM control period. In some cases, both the Rpvs value on which noise generated as a result of starting energization of the heater 40 has been superimposed and the Rpvs value on which noise generated as a result of stopping energization of the heater 40 has been superimposed become larger or smaller than the true element resistance Rpvs. In other cases, the Rpvs value on which noise generated as a result of starting energization of the heater 40 has been superimposed and the Rpvs value on which noise generated as a result of stopping energization of the heater 40 has been superimposed become larger and smaller, respectively, than the true element resistance Rpvs. The CPU 61 can secure accuracy of the Rpvs average by excluding Rpvs values on which noise may be superimposed based on their deviations.

The Rpvs computation processing of the second embodiment will now be described with reference to FIGS. 4 and 5. The CPU 61 reads out a program for the Rpvs computation processing from the ROM 62 and executes the program. The CPU 61 sets a work area in the RAM 63 so as to secure a memory area for Rpvs values including the number of times that the Rpvs values are obtained, their deviations, the buffer for average computation, the cumulating counter, the Rpvs average, the Rpvs timer, and the PWM timer. In the second embodiment, as in the case of the first embodiment, the PWM control cycle (period) of the heater 40 is, for example, 100 ms, and the CPU 61 obtains the Rpvs value at an intervals of, for example, 10 ms.

No window is set before the program for the Rpvs computation processing is executed first time. As shown in FIG. 5, only when the CPU 61 executes the program a first time, the CPU 61 obtains an Rpvs value [P21] one time, and stores the obtained Rpvs value as an Rpvs average A21. Also, the CPU 61 starts the Rpvs timer and the PWM timer, and clears the memory area for a plurality of Rpvs values and their deviations, the buffer for average computation, and the cumulating counter so as to store 0 therein.

Figure 4:
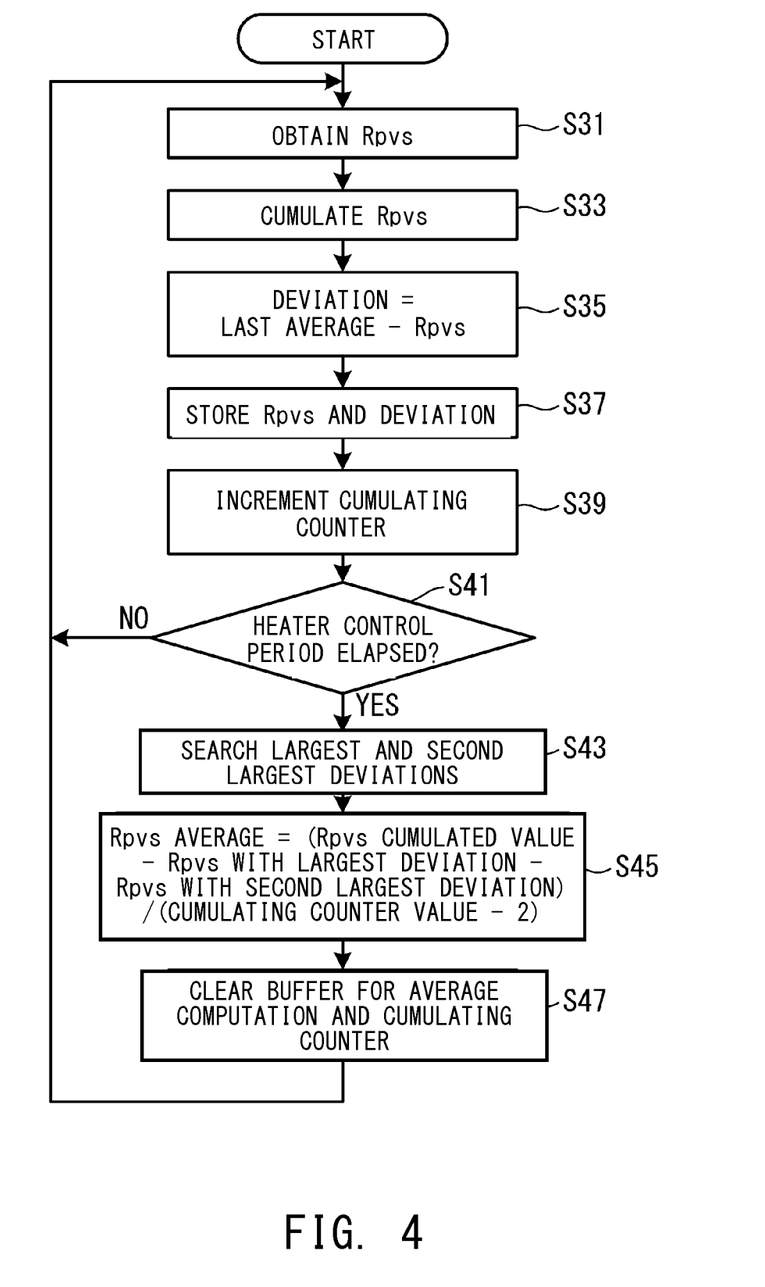
FIG. 4 is a flowchart of Rpvs computation processing (deviation scheme).
Figure 5:
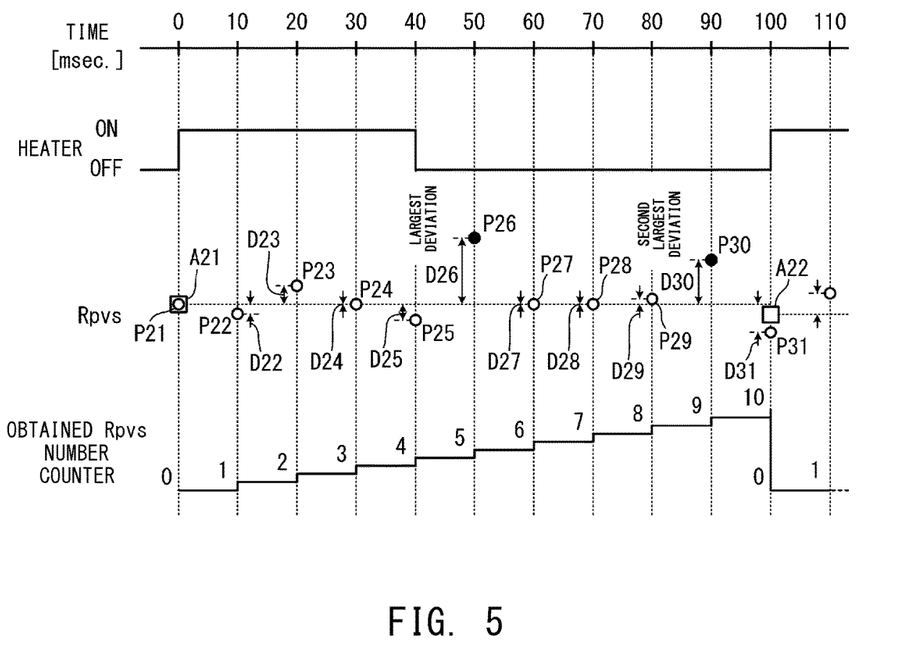
FIG. 5 is a timing chart used for describing the Rpvs computation processing (deviation scheme).

As shown in FIG. 4, as in the case of the first embodiment, the CPU 61 obtains an Rpvs value [P22] (see FIG. 5) calculated based on the potential difference $\Delta$Vs and stores it in the RAM 63 (S31), and restarts the Rpvs timer. The CPU 61 adds the Rpvs value [P22] to the buffer for average computation secured in the RAM 63 (S33). The CPU 61 obtains a deviation [D22] by subtracting the Rpvs value [P22] from the Rpvs average A21 stored in the RAM 63 (S35) and stores it in the RAM 63 while relating it to the Rpvs value [P22] (S37). The CPU 61 increments the cumulating counter (see FIG. 3) by adding one to the count value of the cumulating counter (S39).

The CPU 61 determines whether or not the PWM control period of the heater 40 has elapsed based on the value of the PWM timer (S41). When the PWM control period has not yet elapsed (S41: NO), the CPU 61 returns to S31. Until the PWM control period elapses, the CPU 61 repeats the processing of S31 to S41 to thereby obtain Rpvs values [P23] to [P30], obtain deviations [D23] to [D30], and store them in the RAM 63 in the same manner as described above. The CPU 61 adds the obtained Rpvs values to the buffer for average computation, and increments the cumulating counter.

When 100 ms has elapsed after start of the PWM timer, the CPU 61 adds the obtained Rpvs value [P31] to the buffer for average computation (S33), obtains its deviation [D31] (S35), stores it together with the Rpvs value [P31] (S37), and increments the cumulating counter (S39). When the CPU 61 determines based on the value of the PWM timer that the PWM control period has elapsed (S41: YES), the CPU 61 restarts the PWM timer. The CPU 61 searches for the largest and second largest deviations from the plurality of deviations [D22] to [D31] stored in the RAM 63 and related to the plurality of Rpvs values [P22] to [P31] (S43). In the example of FIG. 5, the deviation [D26] of the Rpvs value [P26] obtained when 50 ms has elapsed after the start of the PWM timer is the largest, and the deviation [D30] of the Rpvs value [P30] obtained when 90 ms has elapsed after the start of the PWM timer is the second largest. The CPU 61 subtracts the Rpvs value [P26] and the Rpvs value [P30] from the total of the Rpvs values [P22] to [P31] cumulatively added to the buffer for average computation. Also, the CPU 61 subtracts 2 from the value of the cumulating counter. The CPU 61 calculates an Rpvs average A22 by dividing the value of the buffer for average computation after the subtraction by the value of the cumulating counter after the subtraction (S45). The CPU 61 stores the calculated Rpvs average A22 in the RAM 63. Also, the CPU 61 copies the Rpvs average A22 to a predetermined memory area of the RAM 63 so as to allow another program which is executed by the CPU 61 for PWM control of the heater 40 to utilize the Rpvs average A22. The CPU 61 clears the buffer for average computation and the cumulating counter to thereby store 0 therein (S47), and returns to S31.

After that, in the same manner as described above, the CPU 61 obtains a plurality of Rpvs values in each PWM control period, and obtains the Rpvs average for the present PWM control period while excluding two Rpvs values whose deviations from the Rpvs average obtained in the last PWM control period are the largest and the second largest. When the CPU 61 executes another program, it calculates the duty ratio for the PWM control based on the Rpvs average. The CPU 61 controls the heater control circuit 50 to apply to the heat generation resistor 43 of the heater 40 the voltage Vh having a voltage waveform corresponding to the duty ratio to thereby maintain the temperature of the gas detection element 30 constant. Since the Rpvs average is obtained from a plurality of Rpvs values during a single PWM control period from which Rpvs values influenced by noise have been removed, the accuracy of the Rpvs average is high, and the CPU 61 can control the temperature of the gas detection element 30 accurately. As in the case of the first embodiment, considering that in some cases each of the noise generated when energization of the heater 40 is started and stopped affects the Rpvs value one time, it is sufficient for the CPU 61 to obtain at least four Rpvs values and compute the Rpvs average one time in each PWM control period.

As described above, the CPU 61 of the ECU 100 can obtain the Rpvs average used for control of energization of the heater 40 while excluding an Rpvs value(s) which may have been influenced by noise or the like. Noise or the like is apt to be generated when energization of the heater 40 is started or stopped. The CPU 61 can obtain the Rpvs average accurately, even when the CPU 61 obtains an Rpvs value(s) influenced by noise. Therefore, it is unnecessary for the CPU 61 to perform the control of obtaining the Rpvs values while avoiding timings at which the energization of the heater 40 is started and stopped. Therefore, the processing can be simplified. Also, since the CPU 61 is not required to detect the timings at which the energization of the heater 40 is started and stopped, the CPU 61 can always perform the operation of obtaining the Rpvs values.

Also, by excluding an Rpvs value(s) which does not fall within a window that is set based on the Rpvs average (reference) or excluding two Rpvs values whose deviations from the Rpvs average are the largest and the second largest, the CPU 61 can easily exclude the Rpvs value(s) which may have been affected by noise or the like and can obtain the Rpvs average accurately in each of the above-described cases. By controlling energization of the heater 40 using an accurate Rpvs average, the CPU 61 can heat the gas detection element 30 at a proper temperature, and, consequently, can accurately detect the air-fuel ratio of exhaust gas based on the oxygen concentration thereof.

Notably, the present invention is not limited to the above-described embodiments, and may be modified in various ways without departing from the spirit and scope of the claims appended hereto.

For example, in the above embodiments, the sensor control apparatus is an ECU of an automobile. However, a control apparatus independent from the ECU may be provided. The gas sensor exemplified in the embodiments is a full range air-fuel ratio sensor; however, the present invention may be applied to other types of gas sensors which include a gas detection element whose substrate is a solid electrolyte body and a heater element which heats the solid electrolyte body for quick activation; e.g., an oxygen sensor, an NOx sensor, an HC sensor, etc. In the above-described embodiments, the element resistance is detected using a voltage change at the time when a current having a specific magnitude is supplied to a specific cell (the Vs cell 38 in the above-described embodiments). However, the element resistance may be detected using a current change at the time when a voltage having a specific magnitude is applied to a specific cell. Notably, the specific cell for detecting the element resistance is not limited to the Vs cell 38, and may be applied to other cells (the Ip cell 37 in the above-described embodiments).

In the above-described embodiments, the PWM control period is set to 100 ms. However, the length of the PWM control period may be freely set. In the above-described embodiments, the Rpvs obtaining interval is set to 10 ms. However, the Rpvs obtaining interval may be freely set so long as at least four Rpvs values can be obtained during a single PWM control period. Notably, the PWM control period is not required to be n times the Rpvs obtaining interval (period) where n is an integer. In the embodiments, the PWM control period is clocked by the PWM timer provided by the Rpvs computation processing. However, the method of detecting elapse of the PWM control period is not limited thereto. For example, the embodiments may be modified such that the CPU 61 outputs a signal (e.g., brings a flag or the like to an on or off state) notifying elapse of the PWM control period in another program in which the CPU 61 performs the PWM control, and the CPU 61 receives that signal in the Rpvs computation processing to thereby detect elapse of the PWM control period.

In the embodiments, the CPU 61 performs the Rpvs computation processing and obtains the Rpvs average so as to use it for calculating the duty ratio used for the PWM control, in a temperature constant control performed for stabilizing operation after activation of the gas detection element 30. However, the CPU 61 may use the Rpvs average for temperature control in a transition period during which the heater 40 heats the gas detection element 30 for activation.

In the first embodiment, the width of the window (the upper limit value and the lower limit value) is obtained by adding a predetermined value to the Rpvs average (reference) and subtracting the predetermined value from the Rpvs average. However, the difference between the upper limit value and the Rpvs average may differ from the difference between the lower limit value and the Rpvs average. For example, in the case where the Rpvs average is used for temperature control for activating the gas detection element 30, the window may be set such that the difference between the lower limit value and the Rpvs average becomes larger than the difference between the upper limit value and the Rpvs average. This is because the element resistance Rpvs is apt to decrease as the temperature of the gas detection element 30 rises.

In the second embodiment, two Rpvs values whose deviations from the Rpvs average are the largest and the second largest are excluded from the Rpvs values used for calculating the Rpvs average. However, the number of the Rpvs values excluded from the Rpvs values used for calculating the Rpvs average is not limited two and may be three or more.

This application is based on Japanese Patent Application No. 2013-196595 filed Sep. 24, 2013, incorporated herein by reference in its entirety.

What is claimed is:

1. A heater control apparatus for a gas sensor which includes a gas detection element having at least one cell composed of a solid electrolyte member and a pair of electrodes provided thereon, and a heater which generates heat upon energization so as to heat and activate the gas detection element, the heater control apparatus controlling energization of the heater in a plurality of energization periods and comprising:

detection means for detecting the resistance of the gas detection element as an element resistance;

extraction means for extracting element resistance values which satisfy a predetermined condition from a plurality of element resistance values detected by the detection means;

computation means for computing an average of the element resistance values extracted by the extraction means; and heater control means for setting a heater energization duty ratio on the average computed by the computation means and periodically starting and stopping energization of the heater, wherein the detection means is configured to detect at least four element resistance values within individual energization periods during which the heater is energized by the heater control means;

the computation means is configured to compute the average in individual energization periods within which the heater is energized by the heater control means; and the element resistance values which satisfy the predetermined condition are (i) element resistance values which are a portion of the element resistance values detected during a present energization period and which fall within a range having a predetermined value based on the average that is computed by the computation means in a last energization period, or (ii) element resistance values which are a portion of the element resistance values detected during the present energization period and which remain after exclusion of two element resistance values which are the largest and the second largest in terms of the difference from the average computed by the computation means in the last energization period.

2. The heater control apparatus according to claim 1, wherein the element resistance values which satisfy the predetermined condition are (i) the element resistance values which are the portion of the element resistance values detected during the present energization period and which fall within the range having the predetermined value based on the average that is computed by the computation means in the last energization period.

3. The heater control apparatus according to claim 1, wherein the element resistance values which satisfy the predetermined condition are (ii) the element resistance values which are the portion of the element resistance values detected during the present energization period and which remain after exclusion of two element resistance values which are the largest and the second largest in terms of the difference from the average computed by the computation means in the last energization period.

* * * * *